United States Patent [19]

Ishikawa et al.

[11] Patent Number: 4,596,806
[45] Date of Patent: Jun. 24, 1986

[54] 7-PIPERIDINO-1,2,3,5-TETRAHYDROIMIDAZO[2,1-B]-QUINAZOLIN-2-ONE HAVING PLATELET AGGREGATION INHIBITORY ACTIVITY

[75] Inventors: Fumiyoshi Ishikawa; Shinichiro Ashida, both of Tokyo, Japan

[73] Assignee: Daiichi Seiyaku Co., Ltd., Tokyo, Japan

[21] Appl. No.: 622,596

[22] Filed: Jun. 20, 1984

[30] Foreign Application Priority Data

Jun. 21, 1983 [JP] Japan .................. 58-111498

[51] Int. Cl.$^4$ ................ A61K 31/505; C07D 487/04
[52] U.S. Cl. ................... 514/267; 544/250; 544/284; 546/335
[58] Field of Search ............ 424/251; 544/250; 514/267

[56] References Cited

U.S. PATENT DOCUMENTS

| | | | |
|---|---|---|---|
| 3,932,407 | 1/1976 | Beverung, Jr. et al. | 544/250 |
| 3,983,119 | 9/1976 | Beverung, Jr. et al. | 544/250 |
| 3,983,120 | 9/1976 | Beverung, Jr. et al. | 544/250 |
| 4,208,521 | 6/1980 | Crenshaw et al. | 544/250 |
| 4,256,748 | 3/1981 | Chodnekar et al. | 424/251 |
| 4,455,311 | 6/1984 | Kienzle | 424/251 |

Primary Examiner—Donald G. Daus
Assistant Examiner—Diana G. Rivers
Attorney, Agent, or Firm—Sughrue, Mion, Zinn, Macpeak & Seas

[57] ABSTRACT

7-Piperidino-1,2,3,5-tetrahydroimidazo[2,1-b]-quinazolin-2-one having platelet aggregation inhibitory activity is disclosed. The compound has high water-solubility and reduced influences on the circulatory system.

2 Claims, No Drawings

7-PIPERIDINO-1,2,3,5-TETRAHYDROIMIDAZO[2,1-B]-QUINAZOLIN-2-ONE HAVING PLATELET AGGREGATION INHIBITORY ACTIVITY

FIELD OF THE INVENTION

This invention relates to a novel compound having a blood platelet aggregation inhibitory activity and a salt thereof. More particularly, this invention relates to 7-piperidino-1,2,3,5-tetrahydroimidazo[2,1-b]-quinazolin-2-one of the formula (I):

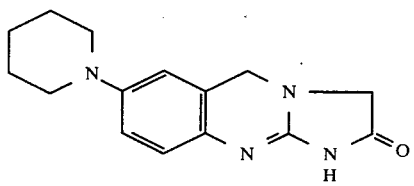
(I)

and a pharmaceutically accetable salt thereof.

BACKGROUND OF THE INVENTION

Known compounds having the same skeleton as the compound of the above-described formula (I) include antihypertensive compounds represented by the formula (II):

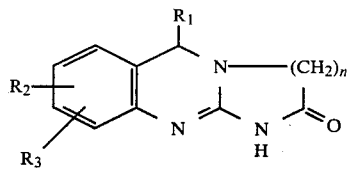
(II)

wherein $R_1$ represents a hydrogen atom, an alkyl group having 1 to 6 carbon atoms; n represents 1 or 2; and $R_2$ and $R_3$, being different from each other, each represents a hydrogen atom, a chlorine atom, a bromine atom, a fluorine atom, a fluoromethyl group, a sulfonic acid group, a hydroxyl group, an alkyl group having 1 to 6 carbon atoms, an alkoxy group having 1 to 6 carbon atoms, a nitro group, an amino group or a phenyl group; or $R_2$ and $R_3$, being the same, each represents a hydrogen atom, a chlorine atom, a bromine atom, a fluorine atom, a hydroxyl group, an alkyl group having 1 to 3 carbon atoms or an alkoxyl group having 1 to 3 carbon atoms; or $R_2$ and $R_3$, being taken together, form a methyleneoxy group or a condensed benzene ring, as disclosed in U.S. Pat. No. 3,932,407 corresponding to Japanese Patent Publication No. 23994/81. The above-mentioned U.S Patent reported that these compounds exhibit a blood platelet aggregation inhibitory activity in addition to the antihypertensive activity.

However, among the above-described known compounds of the formula (II), those having excellent antiplatelet aggregation activity are all sparingly soluble in water and are not, therefore, suitable for parenteral administration. Further, these compounds (II) are characterized by their potent hypotensive activity, and such a hypotensive activity rather exerts a harmful influence on the circulatory system when applied in the therapy of thromboembolia making use of their platelet aggregation inhibitory activity.

Also, U.S. Pat. No. 4,256,748 discloses imidazo[2,1-b]quinazolin-2(3H)-ones which are useful for treating and prophylaxis of cardiac insufficiency and cardiac failure, but these compounds have a substituent such as an alkyl group at the 3-position of the imidazo[2,1-b]quinazolin skeleton and their activity is different from that of the compound of this invention.

SUMMARY OF THE INVENTION

The present inventors have conducted extensive studies to eliminate the above-described disadvantages possessed by the known compounds (II), i.e., sparing water-solubility and the adverse influence on the circulatory system, and, as a result, found that the compound represented by the formula (I) is easily soluble in water to exhibit high activity even through parenteral administration and also has but relatively slight influence on the circulatory system while retaining a potent platelet aggregation inhibitory activity, when compared with the above-described compounds (II). It was also found that the compound (I) of the present invention possesses an activity to inhibit metastasis of cancers and an activity to protect against stress-induced gastric ulceration and to stimulate secretion of pancreatic juice and bicarbonates.

DETAILED DESCRIPTION OF THE INVENTION

The compound represented by the formula (I) may be present in the form of tautomers as shown by the following formulae (Ia) and (Ib), but it should be understood that they are also included in the scope of the invention.

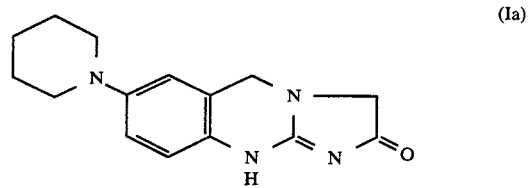
(Ia)

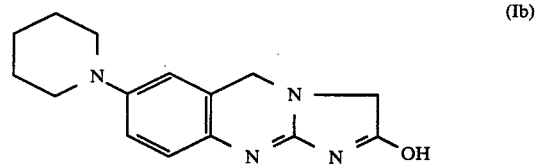
(Ib)

The present invention will be described in detail referring only to the formula (I) for the sake of convenience but not for limitation.

The above set forth excellent activities of the compound of this invention will be illustrated by way of Test Examples. In these Test Examples, all the tests were conducted by using a dihydrochloride monohydrate of the compound (I) [sometimes, simply referred to compound (I)] and, for comparison, 6-methyl-1,2,3,5-tetrahydroimidazo[2,1-b]quinazolin-2-one hydrochloride (BL-3459) and 6,7-dichloro-1,2,3,5-tetrahydro[2,1-b]quinazolin-2-one hydrochloride (BL-4162) that were reported as outstandingly excellent compounds in the above-mentioned U.S. Pat. No. 3,932,407 and 7-amino-1,2,3,5-tetrahydroimidazo[2,1-b]quinazolin-2-one dihydrochloride (BL-7-NH$_2$) which has a similar basic residue as that of the compound (I) and is also described in the same U.S. Patent.

TABLE 1

| Test Compound | Test Example 1 Solubility Test | |
|---|---|---|
| | Water-Solubility (mg/ml) | |
| | Tap Water* | Water at pH 4 |
| Compound (I) | 270 | 4.1 |
| BL-3459 | 0.1 | 0.01 |
| BL-4162 | 0.01 | 0.01 |

Note:
*An aqueous solution of each test compound showed a pH of about 2.

As shown in Table 1 above, it was revealed that the compound of the present invention is highly water-soluble and also has a sufficient solubility even in water having a pH value used for parenteral preparations in view of the potency of anti-platelet aggregation activity hereinafter described. Therefore, the compound of the present invention is superior to the known compounds (BL-3459 and BL-4162) in terms of water solubility.

TEST EXAMPLE 2

Test of Platelet Aggregation Inhibition (in vitro)

The test was performed as follows in accordance with the method of Ashida et al, *Thrombosis and Haemostasis*, Vol. 40, p542 (1979).

Blood was taken by puncture from the heart of a Wistar Imamichi rat under anesthesia with pentobarbital into a syringe containing 1/10 volume of a 3.13% aqueous solution of sodium citrate dihydrate, and the citrated blood was centrifuged to obtain a platelet-rich-plasma (PRP). In the same manner, citrated blood was collected from the vein of a healthy human who had not taken aspirin or any other anti-inflammatory agent since before 10 days, followed by centrifugation to obtain PRP. 0.005 ml of each test compound was added to 0.445 ml each of these PRP samples, and the system was warmed at 30° C. for 1 minute. 0.05 ml of an aggregation inducer (ADP or collagen) was then added thereto, and platelet aggregation was determined according to the method of Born, *Nature*, Vol. 194, p927 (1962). The inhibitory activity of platelet aggregation was expressed in terms of 50% inhibition concentration, and the results obtained are shown in Table 2.

TABLE 2

| Test Compound | Platelet Aggregation Inhibitory Activity (in vitro: $IC_{50}$ μM) | | |
|---|---|---|---|
| | Origin of Blood | Aggregation Inducer | |
| | | ADP | Collagen |
| Compound (I) | human | 2.5 | 0.53 |
| | rat | 3.8 | 0.33 |
| BL-3459 | human | 1.7 | 0.7 |
| | rat | 5.0 | 0.76 |
| BL-4162 | human | 1.2 | 0.5 |
| BL-4162 | rat | 0.8 | 0.02 |
| BL-7-$NH_2$ | human | 50 | 28 |
| | rat | 170 | 16 |

As is apparent from the results of Table 2, the compound of the present invention exhibits anti-platelet aggregation activity substantially equal to that of BL-3459 and BL-4162 which had been reported to have potent activity.

In addition, BL-7-$NH_2$ having a basic residue scarcely exhibits platelet aggregation inhibitory activity.

TEST EXAMPLE 3

Test of Platelet Aggregation Inhibition (ex vivo, p.o.)

Each test compound was dissolved or suspended in a 0.5% Tween 80 aqueous solution and orally administered to 5 male Wistar Imamichi rats (body weight: about 270 g) per group which had been fasted overnight at a dose of 10 mg/Kg or 1.0 mg/Kg. One hour later, citrated blood was taken from the heart, and platelet aggregation was determined in the same manner as described in Test Example 2. The results obtained are shown in Table 3.

TABLE 3

| | Platelet Aggregation Inhibitory Activity (ex vivo: % inhibition) | | |
|---|---|---|---|
| | | Aggregation Inducer | |
| Test Compound | Dose (mg/Kg) | ADP (%) | Collagen (%) |
| Compound (I) | 10 | 33.8* | 59.5* |
| | 1 | 16.8 | 20.6* |
| BL-3459 | 10 | 31 | 54 |
| | 1 | 12 | 41 |
| BL-4162 | 10 | 8 | 53 |
| | 1 | 10 | 33 |

Note:
*$P < 0.05$

It can be seen from Table 3 that the compound of the present invention showed a significant aggregation inhibitory activity in either ADP- or collagen-induced aggregation at a dose level either of 10 mg/Kg or 1 mg/Kg, whereas the activity of the comparative compounds (BL-3459 and BL-4162), though somewhat displayed, widely varied depending on the individual animal and, therefore, cannot be regarded significant. This proves that the compound of the present invention produces a reliable effect when orally administered to animals.

TEST EXAMPLE 4

Test of Platelet Aggregation Inhibition (ex vivo; i.v.)

As test animals, 5 male Wistar-Imamichi rats (body weight: about 270 g) that had been allowed food and water ad libitum were used per group. The test compound was dissolved in a physiological saline solution (J.P.) and continuously injected to the rats under anesthesia with pentobarbital through the femoral vein. 15 minutes later, citrated blood was taken from the heart, and platelet aggregation was determined in the same manner as in Test Example 2. The results are shown in Table 4 below.

TABLE 4

| | Platelet Aggregation Inhibitory Activity (in vivo: % inhibition) | | |
|---|---|---|---|
| | | Aggregation Inducer | |
| Test Compound | Dose (mg/Kg/min) | ADP (%) | Collagen (%) |
| Compound (I) | 0.067 | 37** | 100*** |
| | 0.02 | 11 | 86** |

Note:
**$P < 0.01$
***$P < 0.001$

It was confirmed from the results of Table 4 that the compound of the present invention possesses a sure and significant activity to inhibit platelet aggregation at extremely low doses. This can be one of and the greatest of excellent characteristics of the compound of the present invention from the fact that many compounds having platelet aggregation inhibitory activity are known but none of them exerts such kind of platelet aggregation inhibitory activity through intravenous administration.

In particular, in the therapy of acute thromboembolism, it is impossible to give patients drugs through oral administration since many of them are unconscious due to attack. Hence, it is of great significance that the compound of the present invention proved a possibility of intravenous administration and its effectiveness.

TEST EXAMPLE 5

Test of Influence on Circulatory System 5 or 6 male normal SLC-Wistar rats per group (body weight: 205–255 g) orally received 50 mg/Kg of the test compound, and the blood pressure (tail cuff method) and the heart beats were measured with the passage of time in order to elucidate influences of the test compound on the circulatory system. The results obtained are shown in Table 5.

TABLE 5

| | Test Compound | | |
|---|---|---|---|
| | Compound (I) | BL-3459 | BL-4162 |
| Initial Blood Pressure (mmHg) | 132 ± 2.5 | 129 ± 2.4 | 130 ± 3.2 |
| Reduction in Blood Pressure (%) | | | |
| Time After Admin. (hr) | | | |
| 1 | 18** | 23** | 11* |
| 2 | 12** | 28** | 16* |
| 3 | 12* | 26** | 17** |
| 4 | — | — | 14** |
| 5 | 12* | 34** | 14** |
| 6 | 9 | 35** | 13* |
| 24 | — | 12* | — |

| | Test Compound | | |
|---|---|---|---|
| | Compound (I) | BL-3459 | BL-4126 |
| Initial Heart Beat (beat/min) | 381 ± 10 | 464 ± 10.3 | 377 ± 13.9 |
| Increase in Heart Beat (%) | | | |
| Time After Admin. (hr) | | | |
| 1 | 27** | 18** | 28* |
| 2 | 32** | 20** | 37** |
| 3 | 27* | 17** | 31** |
| 4 | — | — | 37** |
| 5 | 25* | 18** | 31** |
| 6 | 17* | 19* | 31** |

Note:
*P < 0.05
**P < 0.01
Initial values represent mean ± S.E.

It can be seen from the results shown in Table 5 above that the reduction in blood pressure and increase in heart beat caused by the compound of the present invention are relatively small and also these changes can be restored in short periods of time. This indicates reduced influences of the present compound upon the circulatory system as compared with the comparative compounds (BL-3459 and BL4162).

TEST EXAMPLE 6

Test of Inhibition of Platelet Aggregation Caused by Cancer Cells (in vitro)

Blood was taken from the abdominal vein of a 7-week-old C57BL/6 male mouse into a syringe containing 1/10 volume of a 3.13% aqueous solution of sodium citrate dihydrate as an anticoagulant. The thus prepared citrated blood sample was centrifuged at 230×g at room temperature for 7 minutes. The resulting supernatant fluid was used as PRP. The remainder was further centrifuged at 1,500×g at room temperature for 10 minutes, and the supernatant fluid was used as platelet-poor-plasma (PPP). Platelet count in PRP was adjusted to 450,000 per mm$^3$ by PPP. A 450 μl of PRP was placed in a reaction tube and subjected to centrifugation at 950 rpm at 30° C. About 1 minute later while continuing the centrifugation, 5 μl of a 200 mM calcium chloride aqueous solution was added to the system to a final concentration of 2 μM. 30 seconds later, 5 μl of a saline solution of the compound (I) (dihydrochloride monohydrate) was added to the system, and additional 30 seconds later, 50 μl of a cell suspension containing 1×10$^5$ cells of B16 melamona BL6 (B16BL6) originated in a C57BL mouse or 50 μl of a cell suspension containing 1×10$^6$ cells of Lewis lung cancer (3LL) originated in a C57BL mouse was added thereto. Platelet aggregation of the sample system was determined from changes in transmittancy by use of an aggregometer.

The above-described cell suspensions were prepared according to the method of Tanaka et al., *Invasion and Metastasis*, 2: 289 (1982).

The test results revealed that the compound of the present invention completely inhibited platelet aggregation due to addition of B16BL6 cells at a final concentration of 3 μM or more and platelet aggregation due to addition of 3LL cells at a final concentration of 1 μM or more, and partially inhibited aggregation induced by both cells at a concentration of 0.3 μM.

TEST EXAMPLE 7

Test of Inhibition of Platelet Aggregation Caused by Cancer Cells (ex vivo)

The compound of the invention (dihydrochloride monohydrate) dissolved in a physiological saline solution (J.P.) was intravenously or orally administered to a 7-week-old C57BL/6 male mouse (body weight: about 20 g). Three minutes after the intravenous administration or 1 hour later from the oral administration, blood was taken from the abdominal vein into a syringe containing 1/10 volume of a 3.13% aqueous solution of sodium citrate dihydrate and PRP was prepared as described before in Test Example 6. The PRP was placed in a reaction tube under the same conditions as in Test Example 6, and 5 μl of a 200 mM calcium chloride aqueous solution was added thereto. One minute later, 50 μl of a B16BL6 (5×10$^4$ cells/50 μl)- or a 3LL (2×10$^6$ cells/50 μl)-cell suspension was added to the system. In the same manner as in Test Example 6, platelet aggregation was determined.

As a result, it was found that the B16BL6-induced aggregation was completely inhibited by the compound of the present invention at a level of 1 mg/kg or more irrespective of the administration route. On the other hand, the 3LL-induced aggregation was delayed 150% or more with 10 mg/kg (i.v.) of the compound of the invention and completely inhibited with 30 mg/kg (i.v.) of the compound of the invention.

TEST EXAMPLE 8

Test of Inhibition of Death by Acute Pulmonary Embolism

The compound of the present invention (dihydrochloride monohydrate) was dissolved in a physiological saline solution (J.P.) and intravenously administered to the tail vein of a 5-week-old (C57BL/6 male mouse (body weight: about 18.5 g) at a dose of 10 mg/kg or 30 mg/kg. After 3 minutes, $5 \times 10^5$ cells of B16BL6 were intravenously inoculated to the tail vein. The death ratios 3 and 10 minutes after the inoculation are shown in Table 6.

TABLE 6

Inhibitory Effect on Death by B16BL6-Induced Acute Pulmonary Embolism

| Dose (mg/kg) | Number of Dead Animals/ Number of Tested Animals | |
|---|---|---|
| | After 3 Min | After 10 Min |
| No treatment | 7/9 | 9/9 |
| 10 | 2/9* | 4/9* |
| 30 | 1/9** | 4/9* |

Note:
The test of significance was evaluated according to Fischer's exact probability test.
*P < 0.05
**P < 0.01

As shown in Table 6, when $5 \times 10^5$ cells of B16BL6 were intravenously inoculated, all the test animals died from pulmonary embolism within 10 minutes after the inoculation. However, administration of the compound of the present invention produced significant inhibitory effects.

TEST EXAMPLE 9

Test of Inhibition on Pulmonary Metastasis $1 \times 10^5$ cells/animal of B16BL6 or $7 \times 10^5$ cells/animal of 3LL were inoculated to the tail vein of 10 to 12 6-week-old C57BL/6 male mice per group (body weight: about 18.5 g). The compound (I) (dihydrochloride monohydrate) dissolved in a physiological saline solution (J.P.) was administered to each animal at a dose of 1, 3 or 10 mg/kg orally 24 hours, 1 hour before and 1 hour after the inoculation, or intravenously immediately before the inoculation. On the 13th day from the inoculation of B16BL6 or 11th day from the inoculation of 3LL, the number of metastatic nodules in the lungs was counted using an operating microscope. The results obtained are shown in Table 7.

TABLE 7

Inhibitory Effect on Hematogeneous Metastasis

| Dose (mg/kg) | Number of Metastatic Nodules in the Lungs | |
|---|---|---|
| | B16BL6 | 3LL |
| No treatment | 9.4 ± 1.6 | 17.2 ± 1.2 |
| 1 | 5.5 ± 1.1* | 15.4 ± 2.8 |
| 3 | 5.3 ± 1.1* | 5.9 ± 1.3* |
| 10 | 6.4 ± 1.1 | 4.0 ± 1.1** |

Note:
The numbers were given as a mean value ± standard error. The test of significance was performed according to a Mann-Whiteney method.
*P < 0.05
**P < 0.01

When a moderate number of tumor cells were intravenously implanted to animals, the animals did not immediately die but metastatic foci were formed in the lungs. As shown in Table 7 before, 9.4±1.6 and 17.2±1.2 (M±SE) of metastatic nodules were observed in the lungs of the mice to which $1 \times 10^5$ cells of B16BL6 were implanted and the mice to which $7 \times 10^5$ cells of 3LL were implanted, respectively. However, the number of metastatic modules was significantly reduced in the treated groups which had orally or intravenously received the compound of this invention before or after the implantation.

As described in the foregoing, the compound of the present invention demonstrated an effect to inhibit metastasis of cancers, which effect being ascribed to inhibition on embolus and thrombus formation in the lungs. Such as metastasis inhibitory activity can be exercised with therapeutic effects when applied to, for example, patients with cancer, before or after operation, in which hematogeneous metastasis is predicted and patients with cancer in which consumptive reduction of platelets and fibrinogen is observed but there is no tendency of hemorrhage.

The $LD_{50}$ values of the compound of the present invention as determined by the probit method are as shown in Table 8.

TABLE 8

| Animal | Sex | $LD_{50}$ (i.v.) (mg/Kg) |
|---|---|---|
| 5-week-old ddy mouse | male | 314.5 |
| | female | 380.0 |
| 5-week-old Wistar rat | male | 232.5 |
| | female | 219.1 |

TEST EXAMPLE 10

Test of Stimulation on Pancreatic Juice Secretion in Dog

Adult mongrel dogs (male and female) having a body weight of 11.8 to 15.8 Kg were anesthetized with Nembutal and Phenobal and a cannula was inserted into pancreatic duct. A solution of Compound (I) dissolved in a physiological saline solution was administered intravenously from femoral vein at a dose of 0.5 ml/Kg. The volume of pancreatic juice was determined in a polyethylene tube connected to the cannula, and the bicarbonate ion concentration in the pancreatic juice was determined by neutralization titration. As a control, a physiological saline solution was administered intravenously. The results obtained are shown in Tables 9 and 10, respectively.

TABLE 9

Activity on Stimulation of Pancreatic Juice Secretion (μl) in Dog

| Test Compound | Time After Administration (min.) | | | | Total |
|---|---|---|---|---|---|
| | 0–15 | 15–30 | 30–45 | 45–60 | 0–60 |
| Control | 222 ± 49 | 237 ± 57 | 223 ± 59 | 241 ± 64 | 923 ± 225 |
| Compound (I) at 100 μg/kg | 323 ± 81 | 223 ± 45 | 178 ± 31 | 226 ± 48 | 950 ± 185 |
| Control | 243 ± 48 | 261 ± 56 | 198 ± 40 | 231 ± 57 | 899 ± 197 |
| Compound (I) at 300 μg/kg | 521 ± 112 | 321 ± 53 | 291 ± 44 | 310 ± 31 | 1444 ± 214 |

TABLE 9-continued

| | Activity on Stimulation of Pancreatic Juice Secretion (μl) in Dog | | | | |
|---|---|---|---|---|---|
| | Time After Administration (min.) | | | | Total |
| Test Compound | 0–15 | 15–30 | 30–45 | 45–60 | 0–60 |
| Control | 310 ± 16 | 283 ± 21 | 262 ± 28 | 250 ± 20 | 1105 ± 76 |
| Compound (I) at 1000 μg/kg | 1363 ± 117** | 573 ± 69** | 455 ± 100 | 414 ± 112 | 2805 ± 225** |

**P < 0.01 (compared with Control)

TABLE 10

Stimulation Activity on Bicarbonate Ion Secretion in Pancreatic Juice in Dog

| | Bicarbonate Ion Concentration (mEq/l)* | Amount of Bicarbonate Ion Secretion (mEq/h)* |
|---|---|---|
| Control | 40.8 ± 1.9 | 38.3 ± 9.9 |
| Compound (I) at 100 μg/kg | 44.5 ± 6.1 | 44.6 ± 9.3 |
| Control | 35.3 ± 3.6 | 33.3 ± 10.4 |
| Compound (I) at 300 μg/kg | 45.8 ± 2.1** | 65.9 ± 9.6 |
| Control | 30.0 ± 3.7 | 33.2 ± 4.5 |
| Compound (I) at 1000 μg/kg | 79.8 ± 5.6*** | 223.7 ± 24.7*** |

*miliequivalent calculated as $HCO_3^-$
**P < 0.05
***P < 0.01

As is apparent from the results shown in Table 9, Compound (I) of this invention did not show any significant activity on the pancreatic juice secretion at a dose of 100 μg/kg (i.v.), whereas, at a dose of 300 μg/kg (i.v.), it increased the secretion to a degree of 214% after 15 minutes and, at a dose of 1000 μg/kg (i.v.), it exhibited significant increases in the secretion to a degree of 440% (after 15 minutes) and 202% (after 30 minutes), as compared with the control (100%). In the total volumes determined after 60 minutes, Compound (I) exhibited an increase to 161% at a dose of 300 μg/Kg (i.v.) and a significant increase to 254% at a dose of 1000 μg/Kg (i.v.), as compared with the control (100%).

Also, as is apparent from the results shown in Table 11, Compound (I) increased the bicarbonate ion concentration in pancreatic juice to 109% at a dose of 100 μg/Kg (i.v.), 130% at a dose of 300 μg/Kg (i.v.) and 266% at a dose of 1000 μg/Kg, as compared with the control, respectively, and the increases at 300 and 1000 μg/Kg were considered significant. In the total output amounts of bicarbonate ions determined 30 minutes after administration, Compound (I) exhibited increases to 116% at a dose of 100 μg/Kg (i.v.), 198% at a dose of 300 μg/Kg and 674% at a dose of 1000 μg/Kg, as compared with the control, respectively, and the increases at 300 and 1000 μg/Kg were considered significant.

TEST EXAMPLE 11

Effect on Water Immersion and Immobilization-induced Gastric Ulcer in Rats

Donryu male rats having a body weight of 352 to 414 g were subjected to the stress-induced gastric ulceration test by water-immersion and immobilization [Takagi and Okabe, Japan J. Pharmacol., 18, 9–18 (1968)] at a water temperature of 20° to 22° C. for 7 hours. Compound (I) was administered orally in the form of a suspension in a 0.5% aqueous CMC solution at a dose of 5 ml/Kg 30 minutes before loading the stress. After the test period, the rats were sacrificed and the hyperemic area and the erosious area on the stomach inside wall were measured to determine % inhibition of the ulcer. The results obtained are shown in Table 11 below.

TABLE 11

| | | | Ulcer Index | | | |
|---|---|---|---|---|---|---|
| Test Compound | Dose (mg/kg, p.o.) | Number of Rat | Hyperemic Area (mm) | Inhibition (%) | Erosious Area (mm) | Inhibition (%) |
| Control (0.5% CMC) | | 7 | 62.1 ± 3.8 | — | 26.2 ± 6.0 | — |
| Compound (I) | 30 | 6 | 19.4 ± 9.0** | 69 | 17.8 ± 5.7 | 32 |
| | 100 | 7 | 0** | 100 | 1.3 ± 0.8** | 95 |
| | 300 | 7 | 0** | 100 | 2.6 ± 1.3** | 90 |

**Significantly different from control group (P < 0.01)

The compound (I) can be produced by reacting a compound represented by the formula (III):

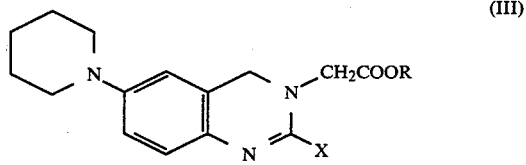

(III)

wherein R represents a lower alkyl group having 1 to 6 carbon atoms, and X represents a halogen atom, e.g., Cl, Br, etc., with ammonia.

The reaction can be advantageously carried out in a sealed tube in the presence of a solvent such as a lower alcohol, e.g., methanol, ethanol, etc., at a temperature of from about 100° C. to about 150° C.

The compound of the present invention can also be prepared by reacting a compound represented by the formula (IV):

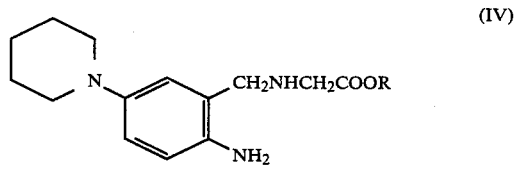

(IV)

wherein R represents a lower alkyl group having 1 to 6 carbon atoms, with a cyanogen halide, such as cyanogen bromide, or N-amidinopyrazole.

The above reaction can be advantageously carried out in a solvent such as a lower alcohol, e.g., methanol, ethanol, etc., under reflux or at room temperature followed by treating the reaction mixture with a weak base such as sodium bicarbonate or sodium carbonate.

The starting compounds of the formulae (III) and (IV) can be prepared according to the reaction scheme shown below:

stearate, calcium hydrogenphosphate, talc, vegetable oils, polyalkylene glycols and the like.

Various dosage forms of the therapeutic agents can be selected according to the purpose of the therapy. Typical dosage forms which can be used include tablets, capsules, powders, liquid preparations, suspensions and injectable preparations (solutions, suspensions, etc.).

The compound of this invention and its salts can preferably be administered orally or through intravenous injection. The dosage of the compound is usually about 1 mg to 20 mg per adult human per day in oral

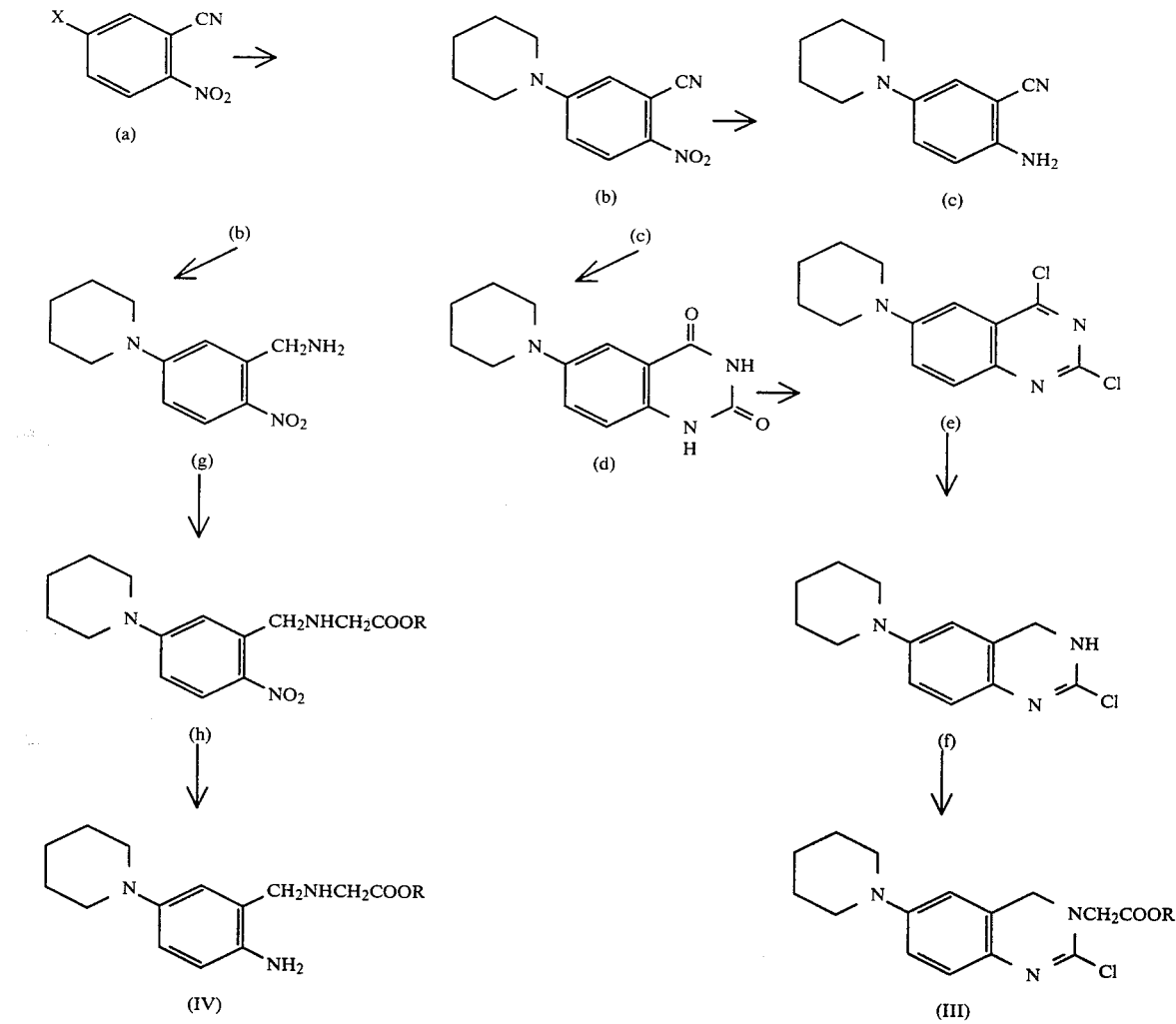

wherein X and R are as defined above.

The compound of the formula (I) thus obtained can be converted into its pharmaceutically acceptable salts with organic or inorganic acids, if necessary. Such salts include a hydrochloride, a hydrobromide, a sulfate, a phosphate, an alkyl- or arylsulfonate, a fumarate, a maleate, a succinate, a citrate and other salts formed with acids commonly employed in the art, with hydrochloride being preferred.

In using the compound of this invention or the salts thereof as therapeutic agents, these compounds can be formulated into pharmaceutical compositions together with ordinary pharmaceutically acceptable carriers selected depending on the type of dosage forms.

Suitable carriers which can be used are, for example, water, gelatin, gum arabic, lactose, starch, magnesium adminstration or about 0.1 mg to 10 mg per adult human per day in intravenous administration.

The present invention will further be illustrated in greater detail with reference to Reference Examples and Examples, but they are not to be construed as limiting the present invention.

REFERENCE EXAMPLE 1

(a) 63.9 g of 5-chloro-2-nitrobenzonitrile was dissolved in 200 ml of dimethylformamide, and 95 ml of piperidine was added to the solution. The mixture was stirred at 50° C. for 30 minutes while externally cooling because of heat generation. The reaction mixture was poured into water, and the precipitate thus formed was collected, washed with water and then with methanol, and dried to obtain 80 g of 2-nitro-5-piperidinobenzonitrile (melting point: 126°–127° C.).

(b) 80 g of the above-obtained benzonitrile derivative was added to a mixture of 700 ml of concentrated hydrochloric acid and 226 g of stannous chloride with stirring while externally cooling, followed by stirring at room temperature for an additional 2 hours. The reaction mixture was poured into ice-water having dissolved therein 700 g of sodium hydroxide, and the precipitated crystals were extracted with chloroform. The extract was washed with water, dried and distilled off to remove the solvent. The residue was purified by silica gel chromatography to obtain 52.2 g of 2-amino-5-piperidinobenzonitrile (melting point: 87°–88° C.).

(c) 50 g of the above-obtained aminobenzonitrile derivative was mixed with 100 g of urea, and the mixture was heated in an oil bath of 180° C. to 210° C. for 2.5 hours. After cooling, the residue was pulverized and washed successively with water, acetone and diethyl ether. Then, the washed powder was added to 300 ml of concentrated hydrochloric acid and refluxed for 3 hours. After cooling, any insoluble matter was removed by filtration, and the filtrate was neutralized with aqueous ammonia to a pH of 7. The precipitate thus formed was filtered, washed successively with water and acetone, and dried to obtain 50 g of crude 6-piperidinoquinazoline-2,4(1H,3H)-dione (melting point: above 280° C.). This product was used as such in the subsequent reaction.

(d) 50 g of the above-described crude dione derivative was converted to its hydrochloride by treating with methanol-hydrochloric acid and added to 500 ml of phosphorus oxychloride. To the resulting mixture, 70 ml of N,N-diisopropylethylamine was added, and the mixture was heat-refluxed for 18 hours. The reaction mixture was concentrated to dryness under reduced pressure, and the residue was poured into ice-water. The precipitate was filtered and extracted with chloroform. The extract was washed with water, dried, and concentrated to dryness under reduced pressure. The residue was purified by silica gel chromatography to obtain 35.4 g of 2,4-dichloro-6-piperidinoquinazoline (melting point: 101°–102° C.).

(e) 33.7 g of the above prepared dichloro derivative was dissolved in 100 ml of chloroform, and 150 ml of ethanol was added thereto. To the solution was further added 22.7 g of sodium borohydride while stirring. The stirring was continued for an additional 30 minutes at room temperature while externally cooling the heat generated. The reaction mixture was dried to a solid under reduced pressure, and water was added to the residue. The insoluble precipitate was collected by filtration, thoroughly washed with water and dried under reduced pressure to give 27.0 g of crude 2-chloro-6-piperidino-3,4-dihydroquinazoline as an amorphous powder. This product was used as it was as a starting material in Example 1.

REFERENCE EXAMPLE 2

(a) A mixture consisting of 2.4 ml of trifluoroacetic acid and 10 ml of tetrahydrofuran was added dropwise to a suspension of 1.2 g of sodium borohydride in 6 ml of tetrahydrofuran under ice-cooling. To the resulting mixture was added a solution of 1.48 g of 2-nitro-5-piperidinobenzonitrile which was prepared in Reference Example 1-(a) in 15 ml of tetrahydrofuran, followed by stirring overnight. 20 ml of a 10% hydrochloric acid aqueous solution was added dropwise to the reaction mixture under ice-cooling, and the resulting mixture was heat-refluxed for 1 hour. The tetrahydrofuran was removed from the reaction mixture by distillation under reduced pressure. The aqueous layer was washed with chloroform, neutralized with sodium hydrogencarbonate and extracted with chloroform. The extracted layer was washed with water, dried and concentrated to dryness under reduced pressure. Purification of the residue by silica gel chromatography gave 1.28 g of 2-nitro-5-piperidinobenzylamine as an oily substance.

(b) A mixture consisting of 1.28 g of the above-obtained benzylamine derivative, 0.29 g of sodium carbonate and 20 ml of dimethylformamide was heated to 80° C. under stirring, and a solution of 0.91 g of ethyl bromoacetate in 20 ml of dimethylformamide was added dropwise to the above mixture over a period of 40 minutes. Thereafter, the mixture was stirred at the same temperature for 1.5 hours, followed by concentration to dryness under reduced pressure. The residue was dissolved in a 5% hydrochloric acid aqueous solution and washed with benzene. The aqueous layer was cooled with ice, rendered alkaline with concentrated aqueous ammonia and extracted with chloroform. The extracted layer was washed with water, dried and then concentrated to dryness under reduced pressure. The residue was subjected to silica gel chromatography to obtain 0.83 g of ethyl 2-nitro-5-piperidinobenzylaminoacetate as an oily substance.

(c) 0.83 g of the ethyl benzylaminoacetate derivative thus obtained was dissolved in 15 ml of ethanol and subjected to catalytic reduction using 20 mg of platinum oxide. After completion of the reduction, the catalyst used was separated by filtration, and the filtrate was concentrated to dryness to yield 0.67 g of ethyl 2-amino-5-piperidinobenzylaminoacetate as an oily substance in a yield of 90%. This crude product was used as such in Example 2.

EXAMPLE 1

27.0 g of 2-chloro-6-piperidino-3,4-dihydroquinazolone was dissolved in 200 ml of methylene chloride, and 19.8 g of ethyl bromoacetate and 1 g of tetrabutylammonium iodide were added to the solution. To the resulting mixture was added 50 ml of a 10N sodium hydroxide aqueous solution in a nitrogen stream under stirring, followed by stirring at room temperature for 1 hours. The reaction mixture was washed with water, dried and distilled off to remove the solvent to obtain crude ethyl 2-chloro-6-piperidino-3,4-dihydro-3-quinazolineacetate as an oily substance in a substantially quantitative yield. The resulting product was added to 100 ml of a 10% ethanol solution of ammonia, and the mixture was heated in a sealed tube at 120° C. to 130° C. for 4 hours. After cooling, the precipitated crystals were filtered, washed with water and dried to obtain 13.0 g of 7-piperidino-1,2,3,5-tetrahydroimidazo[2,1-b]quinazolin-2-one as a free base. This product was suspended in methanol, and concentrated hydrochloric acid was added thereto to adjust to a pH of 1 to 2 thereby forming a solution. The solution was then treated with charcoal, followed by filtration, and the filtrate was concentrated under reduced pressure. The precipitated crystals were collected to give a dihydrochloride monohydrate.

Melting Point: >280° C.

U.V. $\lambda_{max}^{H_2O}$: 198, 248, 275(sh) nm.

IR $\nu_{max}^{KBr}$ cm$^{-1}$: 2800, 2850, 2150, 1775, 1680, 1610, 1595.

$^1$H-NMR (D$_2$O)δ: 1.5–2.2 (6H, m), 3.60 (4H, m), 4.36 (2H, s), 4.86 (2H, s), 7.27, (1H, d), 7.45–7.7 (2H, m).

Elemental Analysis for C$_{15}$H$_{18}$N$_4$O.2HCl.H$_2$O, Calcd.: C, 49.87; H, 6.14; N, 15.51, Found: C, 49.80; H, 6.11; N, 15.56.

EXAMPLE 2

0.64 g of ethyl 2-amino-5-piperidinobenzylaminoacetate was dissolved in 7 ml of ethanol, and to the resulting solution was added a solution of 0.235 g of cyanogen bromide in 2 ml of ethanol, followed by stirring at room temperature overnight. A saturated aqueous solution of sodium hydrogencarbonate was added to the reaction mixture, followed by stirring for 30 minutes. Stirring was further continued at 60° C. for 1 hour, and the precipitated thus formed was filtered, washed with water and dried to obtain 0.46 g of a free base, 7-piperidino-1,2,3,5-tetrahydroimidazo[2,1-b]quinazolin-2-one. It was confirmed that this product was entirely consistent with the product obtained in Example 1.

EXAMPLE 3

| | |
|---|---|
| 7-Piperidino-1,2,3,5-tetrahydro-imidazo[2,1-b]quinazolin-2-one dihydrochloride monohydrate | 30 mg |
| Lactose | 626 mg |
| Corn starch | 300 mg |
| Hydroxypropyl cellulose | 40 mg |
| Magnesium stearate | 4 mg |
| Total | 1,000 mg |

The above components were blended and granulated in a usual manner to prepare tablets each weighing 100 mg.

EXAMPLE 4

300 mg of 7-piperidino-1,2,3,5-tetrahydroimidazo[2,1-b]quinazolin-2-one dihydrochloride monohydrate and 1.0 g of mannitol were dissolved in distilled water for injection to make 100 ml. The solution was filtered using a membrane filter of 0.2μ, placed in vials in 1.0 ml portions, freeze-dried, and sealed to prepare freeze-dried injection preparations.

While the invention has been described in detail and with reference to specific embodiments thereof, it will be apparent to one skilled in the art that various changes and modifications can be made therein without departing from the spirit and scope thereof.

What is claimed is:

1. 7-Piperidino-1,2,3,5-tetrahydroimidazo[2,1-b]quinazolin-2-one and a pharmaceutically acceptable acid addition salt thereof.

2. A platelet aggregation inhibitor comprising a platelet aggregation inhibiting effective amount of 7-piperidino-1,2,3,5-tetrahydroimidazo[2,1-b]quinazolin-2-one as an active ingredient and a pharmaceutically-acceptable carrier.

* * * * *